(12) United States Patent
Friesen et al.

(10) Patent No.: US 12,064,581 B2
(45) Date of Patent: Aug. 20, 2024

(54) RESERVOIR FOR MEDICAL IMPLANTS

(71) Applicant: CraniUS LLC, Baltimore, MD (US)

(72) Inventors: Owen Friesen, Baltimore, MD (US);
Elayna Williams, Baltimore, MD (US);
Ashley Hinga, Baltimore, MD (US);
Charlotte Quinn, Baltimore, MD (US);
John Cai, Baltimore, MD (US); Rahul Gangwani, Baltimore, MD (US);
Conner Delahanty, Baltimore, MD (US)

(73) Assignee: CRANIUS LLC, Baltimore, MD (US)

( * ) Notice: Subject to any disclaimer, the term of this patent is extended or adjusted under 35 U.S.C. 154(b) by 0 days.

(21) Appl. No.: 18/482,152

(22) Filed: Oct. 6, 2023

(65) Prior Publication Data

US 2024/0115843 A1    Apr. 11, 2024

Related U.S. Application Data

(60) Provisional application No. 63/413,740, filed on Oct. 6, 2022.

(51) Int. Cl.
*A61M 31/00* (2006.01)

(52) U.S. Cl.
CPC ....... *A61M 31/002* (2013.01); *A61M 2205/04* (2013.01); *A61M 2207/10* (2013.01); *A61M 2210/0693* (2013.01)

(58) Field of Classification Search
CPC .... A61J 1/10; A61M 3/0262; A61M 5/14276; A61M 5/1428; A61M 5/14586; A61M 5/148; A61M 5/1483; A61M 5/152; A61M 11/008; A61M 31/002; A61M 2025/1054; A61M 2205/04; A61M 2205/075; A61M 2210/0693; A61M 5/14593; A61M 5/1486; A61M 2005/14284; A61M 3/0263; A61M 2205/0693

See application file for complete search history.

(56) References Cited

U.S. PATENT DOCUMENTS

| | | | | | |
|---|---|---|---|---|---|
| 4,412,573 | A | * | 11/1983 | Zdeb | B23P 11/02 604/408 |
| 6,488,652 | B1 | * | 12/2002 | Weijand | A61M 5/14276 604/93.01 |
| 2002/0017310 | A1 | * | 2/2002 | Gruenbacher | A46B 5/04 132/320 |
| 2015/0374964 | A1 | * | 12/2015 | Verhoeven | A61M 5/16804 604/247 |
| 2016/0009455 | A1 | * | 1/2016 | Nakano | B65D 75/5877 383/107 |

(Continued)

*Primary Examiner* — Kami A Bosworth
(74) *Attorney, Agent, or Firm* — Maier & Maier, PLLC

(57) ABSTRACT

A reservoir and method for manufacturing a reservoir that includes a first side piece, a second side piece, an inner fold piece and a reservoir fitting. The first side piece may be sealed to the second side piece with a top seal and a first side seal and a second side seal. The inner fold piece may be sealed to the first side piece and the second side piece through a third side seal, a fourth side seal, and a bottom seal. The top seal may include a fitting opening and the reservoir fitting may be fit into the fitting opening. The reservoir may contain a volume sensing system. The reservoir may be designed so as to empty and fill reliably without any concern for neighboring organ impingement or compression.

8 Claims, 11 Drawing Sheets

(56) References Cited

U.S. PATENT DOCUMENTS

| | | | |
|---|---|---|---|
| 2017/0007759 A1* | 1/2017 | Castropil Logarzo | ........................ A61M 31/007 |
| 2019/0344945 A1* | 11/2019 | Yasuda | ................ B65D 81/266 |
| 2020/0214742 A1* | 7/2020 | Whisler | ............... A61M 3/0262 |
| 2020/0397981 A1* | 12/2020 | Hanson | ............. A61M 5/14276 |

* cited by examiner

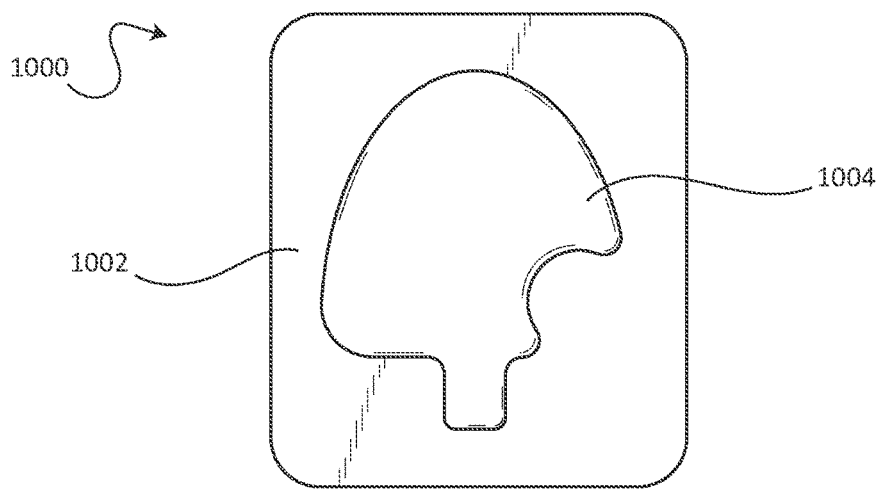
Fig. 10
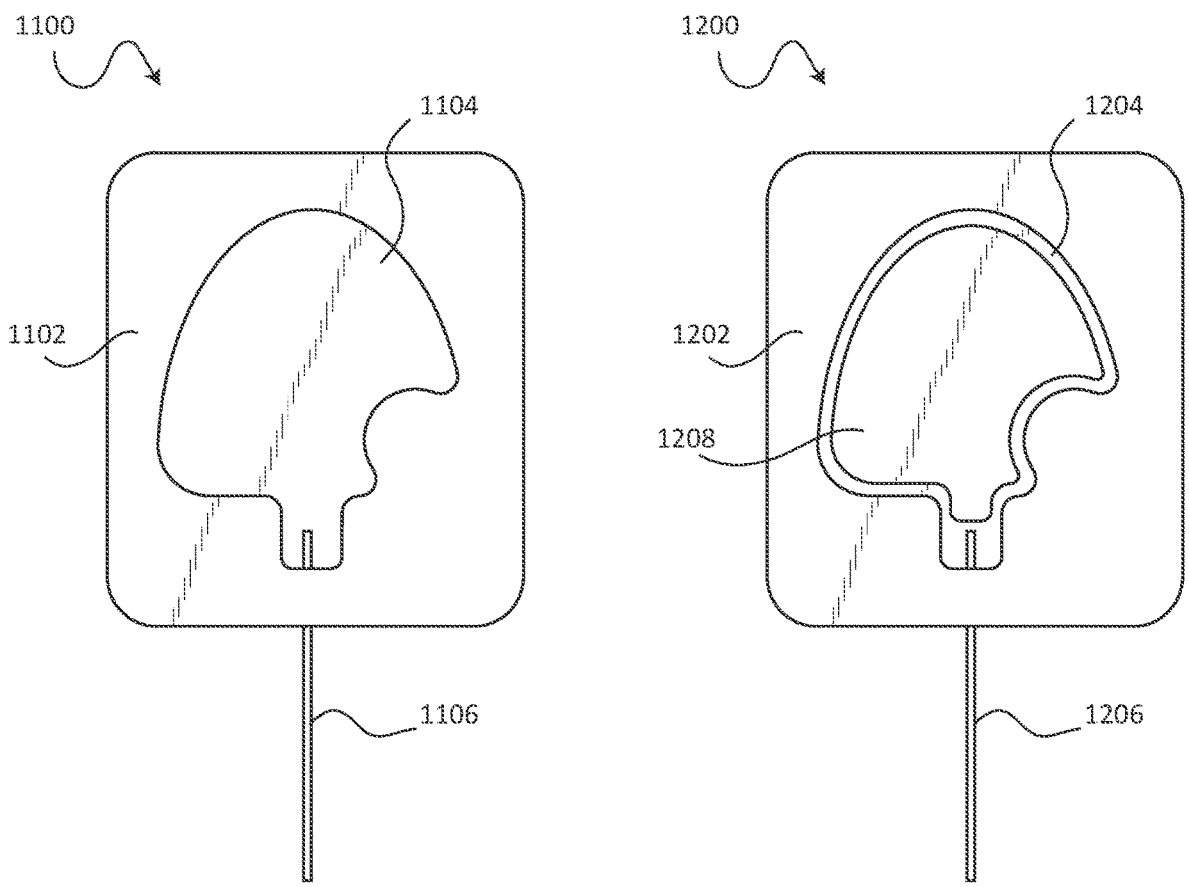
Fig. 11
Fig. 12

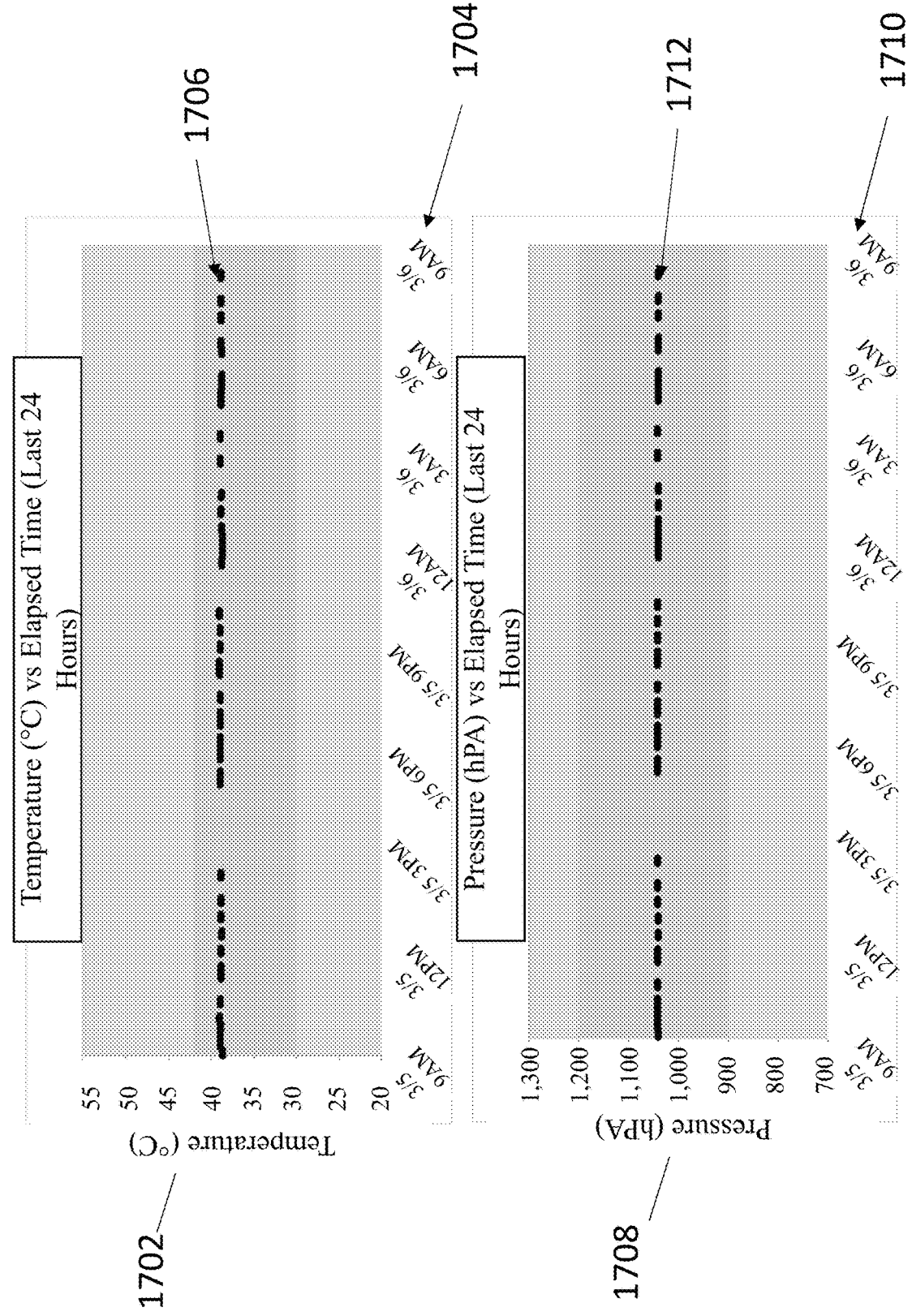

Fig. 18

Pressure (hPA) vs Elapsed Time (Last 24 Hours)

RESERVOIR FOR MEDICAL IMPLANTS

BACKGROUND

The creation and safe use of a medicine delivery device is a longstanding goal of healthcare providers wishing to treat and care for patients suffering from chronic disease. A successful delivery device would reduce required and/or repetitive surgeries, ensure patient compliance and target specific areas of the body. This would improve drug safety and efficacy (in turn reducing the side effects of systemic toxicity), and ease the process of providing lifesaving medicine across tissue barriers (e.g. the blood-brain barrier). Such a device could be an effective tool for chronic disease management when surgery is deemed suboptimal. For instance, some diseases, like brain tumors that invade eloquent areas (which are essential for human functions like speech), cannot be "cut out" by a surgeon and require a non-surgical intervention like direct medicine delivery. There is a critical need to ensure that direct medicine delivery has a consistent dosage that avoids over/under delivery of medicine, because underdosing fails to achieve treatment goals, leading to symptom persistence, and overdosing adds risk for major illness and/or death secondary to lethal toxicity.

Currently, many implantable reservoirs for delivering medicine in the head float freely above the skull, as the components are non-rigid and unable to be placed into a fixed position. As opposed to the chest, abdomen or other extremities, the human head does not have any significant room to work with—given that the thin, soft scalp and hard, immobile skull encapsulate the brain. Pressure above the skull can lead to scalp impingement or wound formation, and pressure below the skull can lead to excessive cortex stimulation and seizures from brain impingement. In addition, this type of anatomical placement can significantly increase the risk of infection as the current reservoir components move around. Micromotion of such craniofacial foreign bodies has been shown to increase risk of foreign body infection and need for premature explanation. Another important aspect that current devices lack is a reconstruction-minded design which follows the curves of the skull—both when the reservoir is empty and when the reservoir is full. Other commonly used medicine reservoirs only have gravity-assisted mechanisms that lack active (i.e. pump assisted) components—and because of this, fail to achieve effective convection-enhanced delivery. Research has consistently shown that localized brain medicine delivery without a pump (e.g. delivered passively through gravity) is futile given the dense brain parenchyma throughout. Equally concerning is that these gravity-assisted mechanisms do not permit adjustable delivery parameters or efficiently monitor delivery of medication—given that there are no volume-sensing mechanisms and/or flowmeters that are small enough to fit within the human head.

Furthermore, many existing implantable medicine delivery devices deliver medicine at a constant rate, which both reduces their ability to react to changing circumstances and can also result in using the medicine more quickly than needed thereby emptying the reservoir prematurely. This type of constant flow delivery is not consistent with the practice and principles surrounding pump-assisted, "convection-enhanced delivery" (CED). The surgeon-scientists at the NIH (Oldfield et al) showed that the brain needs time for relaxation (i.e. alternating period where the medicine delivery pumping system is both "on" and "off"). Thus the ideal reservoir should be able to empty during specific times determined by the care provider. For instance, a reservoir may need to deliver medication for 8 hours per day, and then cease delivery for 16 hours per day to allow the brain time for relaxation in between, something current pumps are incapable of. Moreover, the care provider may require multiple "on" cycles in a 24 hour period, as research helps to elucidate evidence-based regimens based on disease-response. For instance, there could be one 4 hour "on" cycle in the morning, followed by a 4 hour "on" cycle in the evening.

Many existing reservoirs are made of silicone, have a single manufactured material surrounding the drug inside, and/or have porous membranes, which are all suboptimal choices for long-term storage of chemotherapy drugs like Topotecan and TMZ given the risk of permeation or gross leakage. Notably, when a reservoir is coupled with a volume sensing system, any leakage (regardless of rate) could falsely indicate that the device has delivered its life-saving medication to the brain. Chemotherapy agents, such as those used to treat brain tumors, will cause immediate tissue damage and/or a burn injury to any nearby tissues affected by leakage which may lead to major brain damage and/or death. Additionally, many reservoirs cannot be refilled or reloaded without invasive procedures such as repeat surgery. Repeated surgery over time is not safe for the human head. In fact, the more one cuts and incises the scalp for brain surgery and/or filling up a reservoir, the incidence of infection and/or surgical site infections goes up exponentially.

All modern-day implantable medicine delivery devices use a single catheter which chronically empties a unilayer medicine storage reservoir—a simple and straightforward way to perform direct delivery. Unfortunately, a single catheter is limited in how much medicine it can deliver and acts as a single mechanical point of failure for these reservoir systems. Over time, the single catheter may become clogged because scar tissue forms over the end of the catheter where medicine is being delivered to the patient. Furthermore, some diseases of the human brain are unifocal (e.g., an isolated brain tumor lesion) while others are multifocal (e.g. Alzheimer's, Parkinson's disease, Depression, Epilepsy, Schizophrenia, Substance abuse, etc.). A single catheter reservoir system can only deliver medicine to either the left-brain lobe or the right brain lobe, not both, because the corpus provides a barrier to diffusion which divides the two.

Flowmeters are often used to detect the rate of flow in a system, which can provide critical data. Unfortunately, common industrial flowmeters are very large given the mechanical and engineering complexities involved, and have minimum dimensions of around 3-12 inches in length and width. Implantable medical devices do not use these time-tested, industry-standard, integrated flow meters—as the size of these existing flow meters (capable of detecting such small flow rates accurately in microliters) is far too large to fit within existing implants, especially in the temporal skull region. Current engineering challenges have prevented the development of any flow meters of microliter resolution compatible with placement in the human head.

Finally, many existing reservoir systems include metal components such as edge-welded titanium parts or a peristaltic pump system. Ferromagnetic material precludes any type of MRI-compatibility since its material composition can be dangerous within an MRI. Magnetically driven pumps are also incompatible and unsafe with MRI machines. This can lead to a heavily exaggerated image artifact, which is of serious consequence when one wishes to employ MRI imaging for chronic disease assessment and/or tissue response to treatment. This means that there is no safe method to perform imaging check-ups on underlying brain tumors and/or chronic neurologic diseases, which then increases the risk that something is missed. Overall treatment efficacy unquestionably decreases.

SUMMARY

In an exemplary embodiment, the ideal reservoir design and placement for long-term, direct medicine delivery may be within the temporal hard and soft tissue space of the skull.

In an exemplary embodiment, a benefit of the device may be the ability to precisely control and monitor exactly how much of a medicine is being introduced to the specific body part and/or organ on an hourly, daily or weekly basis (i.e. optimized precision improves safety).

In an exemplary embodiment, the novel reservoir may be designed in such a way as to achieve the indirect benefits of real-time flow measurements and overcome a major limitation in implantable medical devices so that the flow precision can be accurately monitored and adjusted.

In an exemplary embodiment the multilayer reservoir system may be designed, so as to allow placement in close proximity to a patient's brain (such as with a long horizontal axis and short vertical axis), and with certain materials which allow full MRI-safety, MRI-compatibility, and MRI-lucency and essential "invisible" characteristics to preserve the modern-day benefits of medical imaging for brain disease management (i.e. allowing the doctors to see if the brain tumor underneath is shrinking or the brain tumor is growing, etc).

In an exemplary embodiment the multilayer reservoir system may be designed to accommodate the size limitations of the human head. Current reservoir systems are circular in design, and fill/open like a balloon in concentric, radial fashion. This type of round form does not work well within the human skull directly over the brain. The ideal reservoir system undergoes predictable shape deformation, filling in a way that is wider than it is tall. This way it can lie safely within an implanted device located within the temporal soft tissue and skull. Dire consequences, such as local organ (i.e. brain) impingement, could and will occur when and if this novel design process is ignored.

BRIEF DESCRIPTION OF THE FIGURES

Advantages of embodiments of the present invention will be apparent from the following detailed description of the exemplary embodiments. The following detailed description should be considered in conjunction with the accompanying figures in which:

FIG. 10 shows an exemplary embodiment of a core mold.

FIG. 11 shows an exemplary embodiment of a reservoir mold with a partial reservoir casing.

FIG. 12 shows an exemplary embodiment of a reservoir mold with a partial reservoir casing and core inserted.

FIG. 17 shows an exemplary graph showing temperature/pressure over time with no fluid flow.

FIG. 18 shows an exemplary graph showing pressure over time with fluid flow.

DETAILED DESCRIPTION

Aspects of the invention are disclosed in the following description and related drawings directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Discussing now FIGS. 1-8, a method for manufacturing a medical device reservoir and a medical device reservoir may be shown and described.

Figure 1:
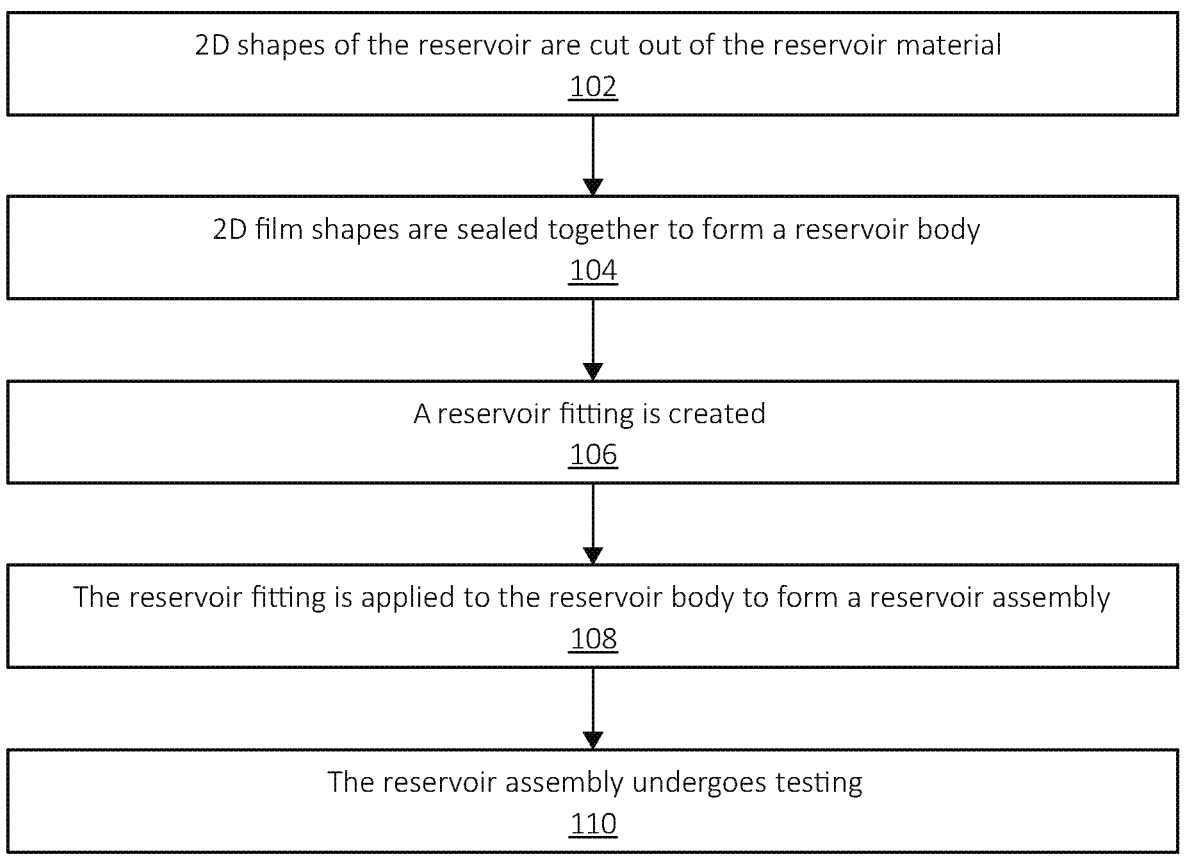
FIG. 1 is a flowchart showing an exemplary method of manufacturing a medical device reservoir.

FIG. 1 is a flowchart showing an exemplary method of manufacturing a medical device reservoir 100. In a first step 102 two-dimensional pieces of the reservoir may be cut out of a sheet of reservoir material. The two-dimensional pieces may include, for example, two side portions and an inner fold portion. The shape of the pieces may be designed using, for example, a computer-aided design (CAD) program. The pieces may then be cut out of the material using, for example, an electronic cutting machine, or may be manually cut out. The reservoir material may be, for example, a metallized polymer film that is MRI-compatible and/or MRI-lucent, and may consist of one or more layers of PET, vacuum metalized PET, and/or LDPE. For example, in an embodiment the film may have a first LDPE layer and a second PET layer. It some embodiments the material may be understood to be very thin, for example less than 10-thousands of an inch in thickness.

In a next step 104 the two-dimensional film pieces may be sealed together to form a three-dimensional reservoir body. In an embodiment the two side pieces may be sealed together along the top edge and a portion of each side edge, and may be sealed to the inner fold portion along the remaining portion of each side edge and a bottom edge. In some embodiments a fitting opening may be left in the top seal seam. The sealing may be done through, for example heat sealing, such as by using a hand wheel heat sealer or an automated heat-sealing machine. In an embodiment the heat sealing may be done at a temperature between 50 and 300° C., or preferably around 150° C. In an embodiment each heat-sealed seam may be, for example, 1-2 mm thick, and each seam may be sealed from one or both sides. In an embodiment using a LDPE layer and PET layer film, the LDPE layer may face inward and the PET layer may face outward. In a next step 106 a reservoir fitting may be created. The reservoir fitting may be, for example, 3D printed out of a stereolithography resin, or may be injection molded out of, for example, polyethylene.

In a next step 108 the reservoir fitting may be bonded to the reservoir body to form a reservoir assembly. The reservoir fitting may be partially inserted into the fitting opening in the sealed reservoir body. The reservoir fitting may then be sealed to the reservoir body, for example in an exemplary embodiment where the reservoir fitting is formed from a thermoplastic such as polyethylene the reservoir fitting may be heat sealed directly into the reservoir for the reservoir assembly. The heat sealing may be done via, for example, a soldering iron or by using a die set to stamp the seal together while applying heat. It may be understood that a die set may have a substantially same geometry as the seam in order to apply an even seal. The die set itself may be utilized as a heating element, or the die set may be applied and the reservoir may be heated by an external heat source, for example an oven. In another exemplary embodiment the reservoir may be fitted using an adhesive, for example by applying Loctite AA or another adhesive with a tool around the section of the fitting that will attach to the reservoir body. Additional adhesive may be applied until there are no open gaps for fluid or air to escape around the fitting.

In a final step 110 the reservoir may be tested after curing. Testing may include, for example, attaching a tube to the reservoir fitting and using a syringe or other device to fill the reservoir with a substance such as DI water. The reservoir may then be inspected for leaks. Additional testing may be done using, for example, a pressure decay leak tester.

Figure 2:
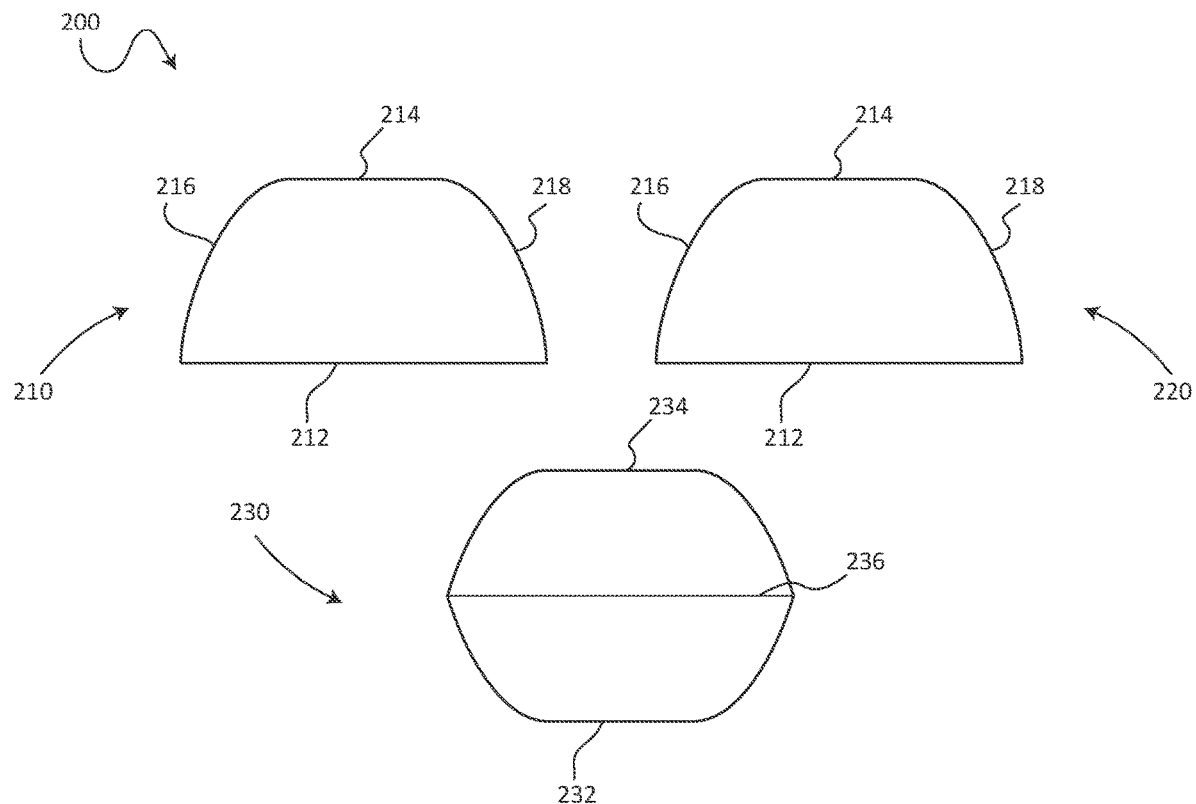
FIG. 2 shows exemplary reservoir cutouts.

FIG. 2 shows exemplary reservoir pieces 200, for example as described in step 102 above. The reservoir pieces 200 may include a first side piece 210, a second side piece 220, and an inner fold piece 230. The first side piece 210 may have a top edge 212, a bottom edge 214, a first side edge 216, and a second side edge 218. The second side piece 220 may have a top edge 222, a bottom edge 224, a first side edge 226, and a second side edge 228. The inner fold piece 230 may have a first edge 232, a second edge 234, and an inner fold 236.

Figure 3:
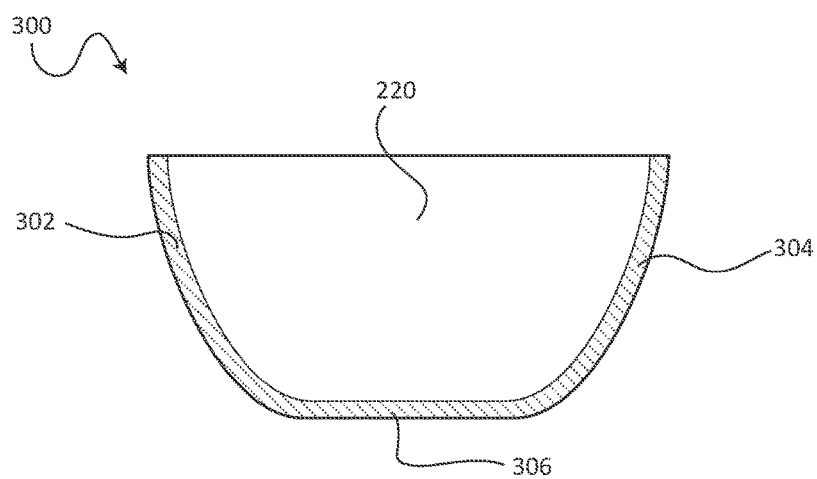
FIG. 3 shows an exemplary partially sealed reservoir.
Figure 4:
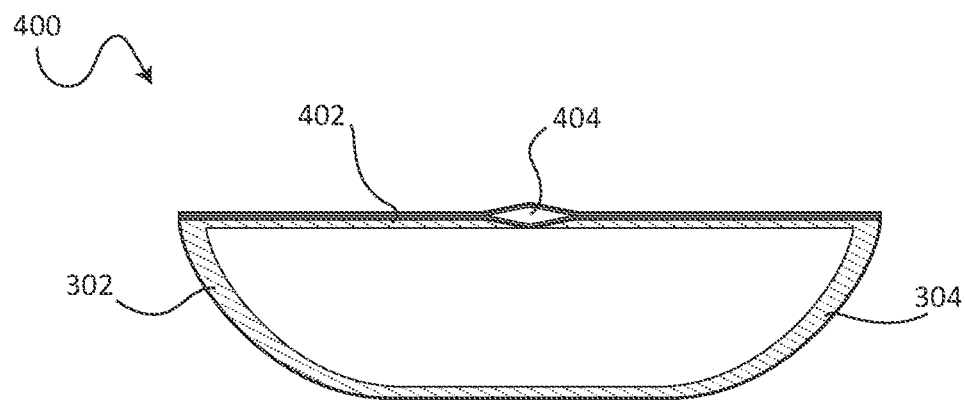
FIG. 4 shows an exemplary sealed reservoir with a fitting opening.

FIG. 3 shows an exemplary partially sealed reservoir 300 with an exemplary side seal 302 another exemplary side seal 304, and an exemplary bottom seal 306. The side seal 302 may be between the first piece first side edge 216, the second piece first side edge 226 and the inner fold piece first edge 232. The second side seal 304 may be between the first piece second side edge 218 the second piece second side edge 228 and the inner fold piece second edge 234. The bottom seal 306 may be between the first piece bottom edge 214 and the inner fold piece first edge 232 and between the second piece bottom edge 224 and the inner fold cutout second edge 234. FIG. 4 shows an exemplary sealed reservoir with a fitting opening 400. The exemplary sealed reservoir 400 may include an exemplary top seal 402 between the first piece top edge 212 and the second piece top edge 222, with an exemplary fitting opening 404.

Figure 5:
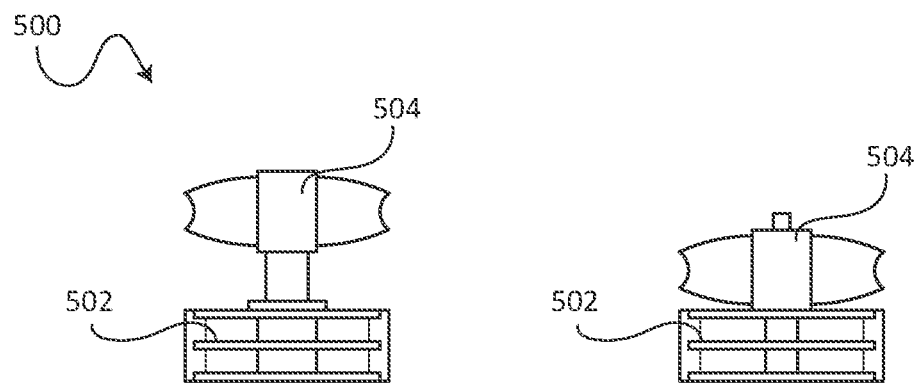
FIG. 5 shows exemplary reservoir fittings.

FIG. 5 shows exemplary reservoir fittings 500. The reservoir fittings 500 may have a reservoir portion 502 which may be inserted into the fitting opening 404 and sealed using, for example heat sealing or adhesive. The reservoir fittings 500 may further include a connection portion 504, which may extend out from the reservoir and allow for connection with external devices including, for example but not limited to, pumps, syringes, catheters, or other medical devices.

Figure 6:
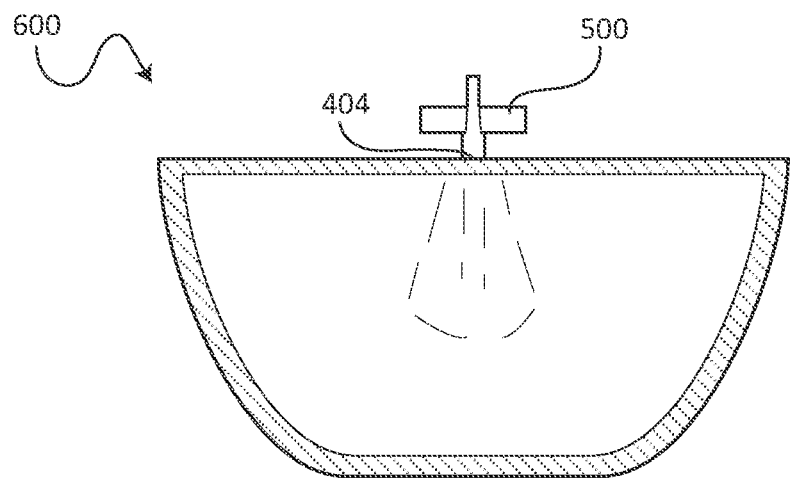
FIG. 6 shows an exemplary reservoir with reservoir fitting.
Figure 7:
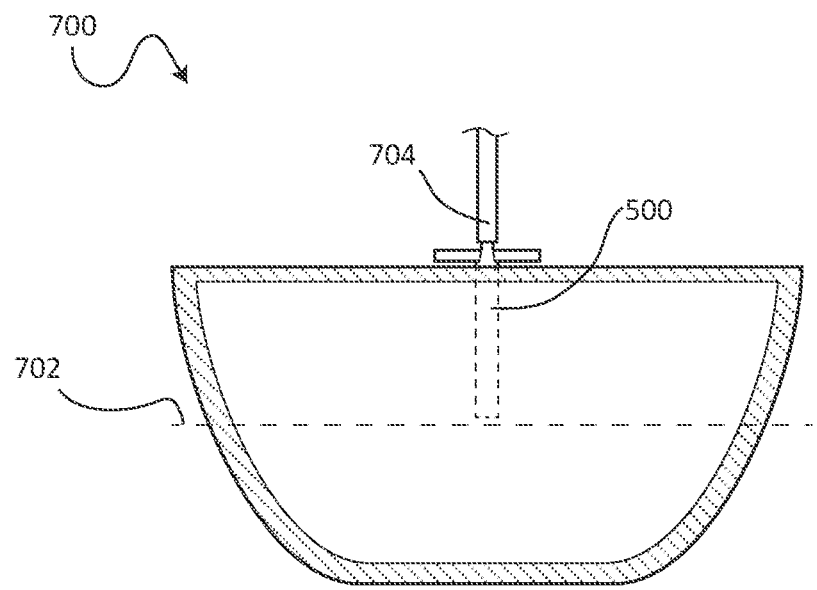
FIG. 7 shows a front view of a completed reservoir.
Figure 8:
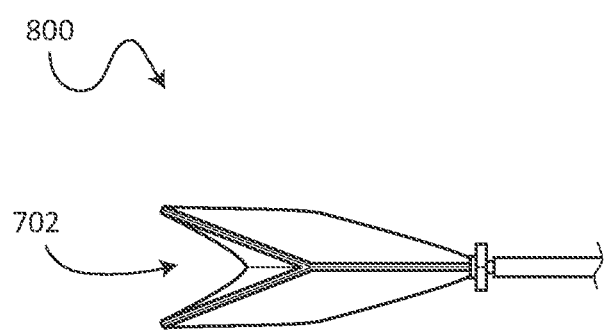
FIG. 8 shows a side view of a completed reservoir.

FIG. 6 shows an exemplary reservoir with reservoir fitting 600. FIG. 7 shows a front view of an exemplary completed reservoir assembly 700. The completed reservoir may have an inner fold 702 and the reservoir fitting 500 may extend into the completed reservoir 700. The completed reservoir may further be connected to an external device, for example a catheter or tube 704. FIG. 8 shows a side view of the completed reservoir 700.

Discussing now FIGS. 9-16, exemplary embodiments of a silicone medical device reservoir and method for manufacturing the exemplary medical device reservoir may be shown and described.

Figure 9:
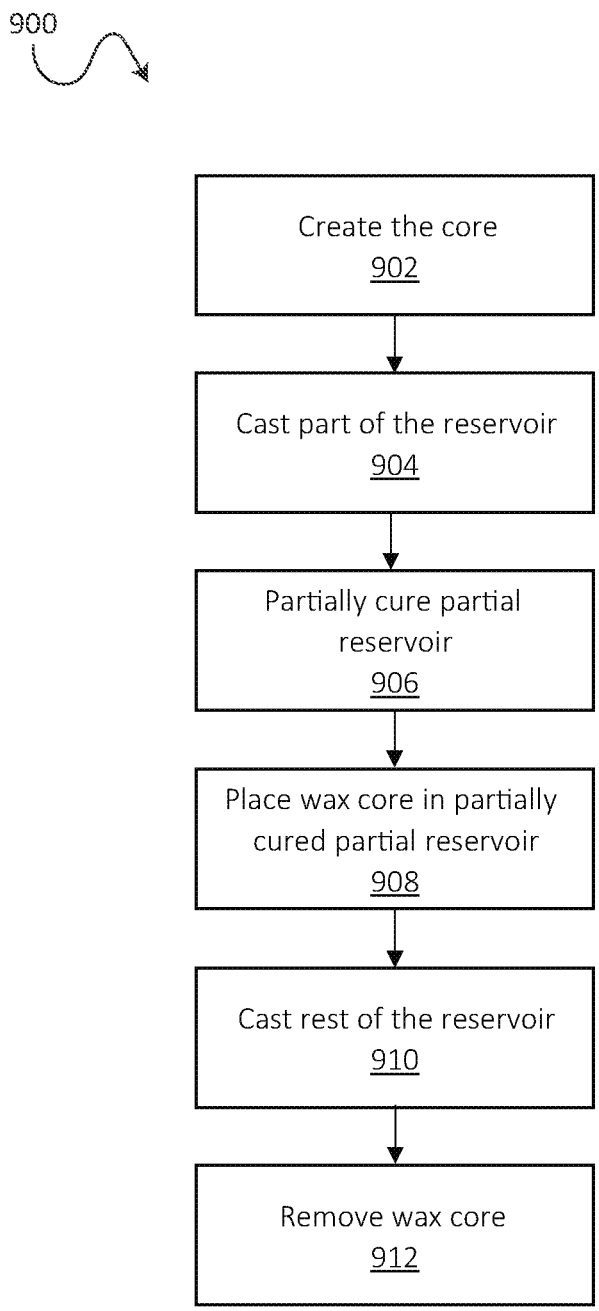
FIG. 9 is a flowchart showing an exemplary method of manufacturing a medical device reservoir.

FIG. 9 is a flowchart showing an exemplary method of manufacturing a first embodiment medical device reservoir 900. The exemplary method of manufacturing a reservoir 900 may begin with creating a core at step 902. At step 904, part of the reservoir casing may be cast. After part of the reservoir casing has been cast 904, the partial reservoir casing may be partially cured 906. At step 908 the core may be placed in the partially cured partial reservoir casing. At step 910, the rest of the reservoir casing may be cast. Finally, the core may be removed in step 912.

FIG. 10 shows an exemplary embodiment of a core mold 1000 and illustrates step 902 in FIG. 1. In an exemplary embodiment the core mold 1000 may include a mold 1002 and a core 1004. In an exemplary embodiment the mold 1002 may be made of biocompatible silicone. In other embodiments the mold 1002 may be made of a different biocompatible material, or multiple layers of materials, including but not limited to, polyethylene, aluminum, latex, butyl rubber, nitrile rubber, or vinyl. In an exemplary embodiment the core 1004 may be made of soy wax. In other embodiments other non-toxic materials with low melting points or soluble characteristics may be used instead. These other materials may include, but are not limited to, paraffin, machinable wax, dissolvable materials such as polyvinyl alcohol and soluble wax, or any other material known by a person having ordinary skill in the art.

In an exemplary embodiment biocompatible silicone may be used. The biocompatible silicone may be a multi-component system, for example, a base material plus a curative material. The biocompatible silicone may be put in one or more syringes, and placed in a centrifuge to be rotated, for example at 1,500 rpm for 2 minutes. Any excess air may need to be purged from the mixture before use, this may be done by, for example, inverting the syringe and purging out extra air.

The core mold may need to be cleaned to remove impurities. In an exemplary embodiment this may be done by, for example, using ultrasonic cleaners with a detergent solution and deionized water.

FIG. 11 shows an exemplary embodiment of a reservoir mold with a partial reservoir casing 1100 and illustrates steps 904 and 906 in FIG. 9. The reservoir mold with a partial reservoir casing 1100 may include a reservoir mold 1102, a partial reservoir casing 1104, and a shaft 1106. In an exemplary embodiment the reservoir mold 1102 may be made of, for example, aluminum, or any other machinable material. In an exemplary embodiment, the partial reservoir casing may be made of biocompatible silicone. In other embodiments, the partial reservoir casing 1104 may be made of a different biocompatible material, including but not limited to, latex, butyl rubber, nitrile rubber, or vinyl. The shaft 1106 may be made of a durable non-toxic material. In an exemplary embodiment this could be, but is not limited to, steel or any other material that can provide stiffness when made into a thin shaft. The shaft may be placed so there is a small space between the end of the shaft and where the bottom of the core will be placed.

In an exemplary embodiment, biocompatible silicone may allow for the reservoir to be safe for use inside a living organism, such as the human body. Furthermore, the biocompatible silicone reservoir may be in direct contact with a drug or payload fluid within a medical implant device. The biocompatible silicone may also be easily moldable and have high thermal resistance. The biocompatible silicone may be flexible, which may reduce the amount of elastic pressure induced on the fluid's contained within, and may prevent a forward-bias state with any one-way valves. In other embodiments, a different biocompatible material may be used, including but not limited to biocompatible polyethylene, parylene, fluoroelastomers, or any other material known to a person having ordinary skill in the art.

The partial curing of the partial reservoir casing 1104 may be done when the partial reservoir casing 1104 is cured enough to hold a core in place, but not cured enough for the core to rise with additional material injection. Consistency may be checked at regular intervals in order to determine when the partial reservoir is sufficiently cured. This may be done for, by example, using tweezers to probe excess material deposited elsewhere. In an exemplary embodiment where the partial reservoir casing 1104 is silicone, the material may be correctly cured when, for example, the silicone lifts up with tweezers, but does not separate and stick to the tweezers.

The reservoir mold 1102 may allow the reservoir to be made into a particular shape. In an exemplary embodiment, the reservoir may be made so the reservoir can be embedded into a head implant or medication dispensing device. In other embodiments, the shape may allow for use in knee replacements hip replacements, shoulder replacements, spine surgery (i.e. chronic pain medicine and/or antibiotic delivery to treat/prevent infection) or any other medical or non-medical device. An exemplary device used here for brain medicine delivery may include numerous embedded technology components as part of a smart-technology embedded mechanical, hardware, and/or software platform with wireless charging capabilities, and hence, the microscopic size constraints of each part inside may be fully accounted for; as each part may fit together like a tightly-woven, puzzle piece with complete mitigation of any unused space. Thus, the reservoir design may address these issues by having a three-dimensional shape that has non-traditional curves and obscure borders.

FIG. 12 shows an exemplary embodiment of a reservoir mold with a partial reservoir casing with core inserted 1200 and illustrates step 908 in FIG. 9. The reservoir mold with a partial reservoir casing with core inserted 1200 may include a reservoir mold 1202, a partially cured partial reservoir casing 1204, a shaft 1206, and a core 1208. The core may be placed so there is an even edge between the core 1208 and the edge of the reservoir mold 1202.

Figure 13:
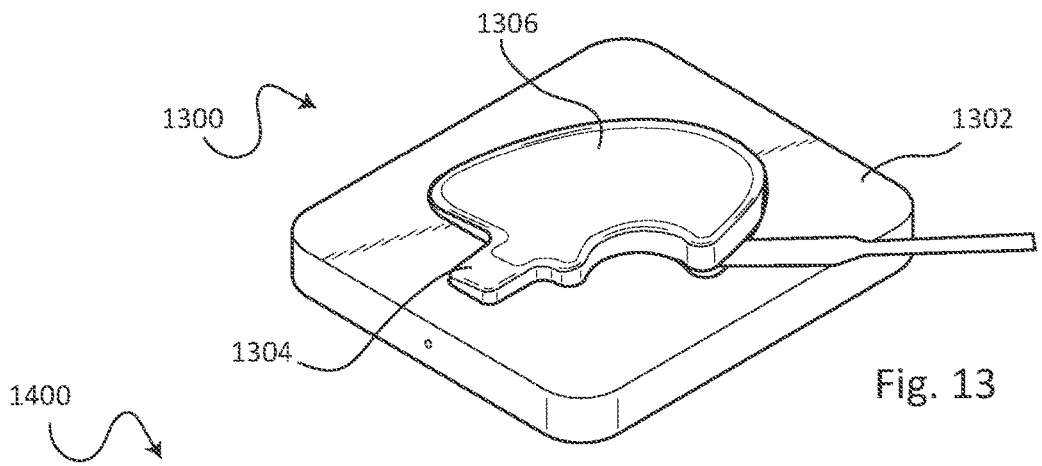
FIG. 13 shows an exemplary embodiment of a reservoir mold with a complete reservoir casing and core inserted.

FIG. 13 shows an exemplary embodiment of a reservoir mold with a complete reservoir casing with core inserted 1300 and illustrates step 910 in FIG. 9. The reservoir mold with a complete reservoir casing with core inserted 1300 may include a reservoir mold 1302, a complete reservoir casing 1304, and a core 1306. The same material used in making the partial reservoir casing may be poured into the reservoir mold 1302 until the mold 1302 is full, creating the complete reservoir casing 1304. The complete reservoir may be allowed to cure completely before being removed from the reservoir mold 1302. The shaft seen in FIG. 12 may also be removed after the curing is complete. After removal from the reservoir mold 1302 there may be a complete reservoir casing 1304 with a core 1306 inside. In other embodiments, the core may be a dissolvable core, or the reservoir may be made by a process that joins two or more reservoir pieces together to create a cavity.

Figure 14:
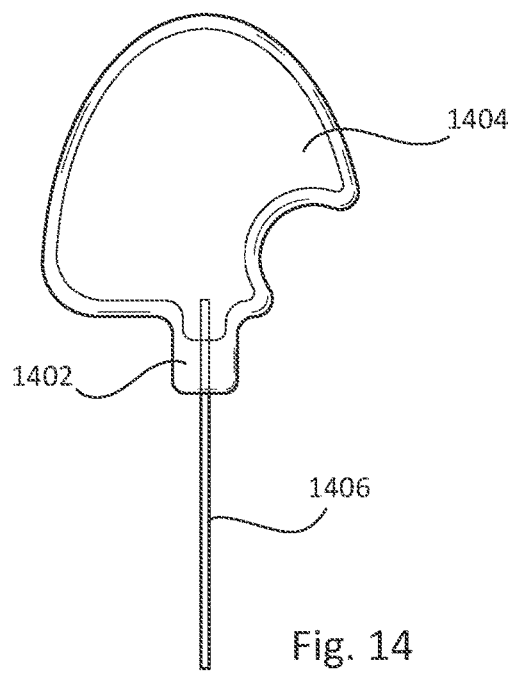
FIG. 14 shows an exemplary embodiment of a reservoir casing with an opening being created.

FIG. 14 shows an exemplary embodiment of a reservoir casing with an opening being created 1400 and illustrates step 912 in FIG. 9. After step 910 as shown in FIG. 13 the complete reservoir casing with core inserted may be heated, for example by being placed in an oven. This heating may be hot enough to melt the core inside, but not hot enough to damage the complete reservoir casing 1402. For example, in an exemplary embodiment, the core may be soy wax, and the reservoir may be heated in an oven at substantially 68° C. for 20 minutes. Once the reservoir is finished being heated, there may be a melted core 1404. There may still be a material layer blocking the opening left by the shaft used in FIG. 13. This layer may be punctured to create an opening, and the puncturing may be done by, in an exemplary embodiment, a steel rod 1406. In other embodiments, another non-toxic durable material may be used, for example, with any other material that can provide stiffness when made into a thin shaft.

Figure 15:
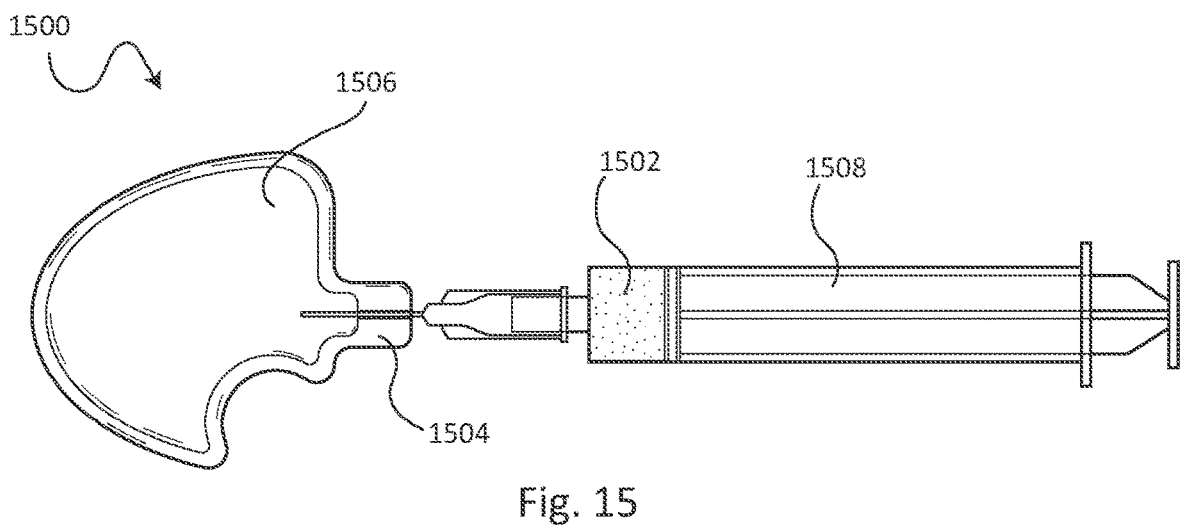
FIG. 15 shows an exemplary embodiment of a reservoir casing with core being removed.

FIG. 15 shows an exemplary embodiment of a reservoir casing with core being removed 1500 and illustrates step 912 in FIG. 9. The heated core 1502 may be removed from the complete reservoir casing 1504, leaving a hollow area 1506. The melted or dissolved core 1502 may be removed by, for example, a syringe 1508.

Figure 16:
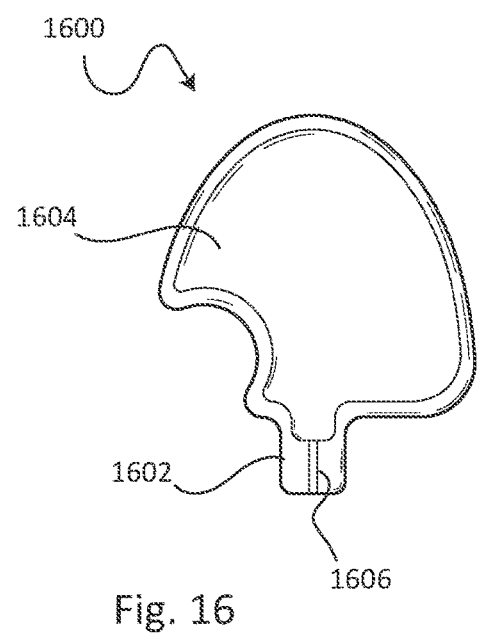
FIG. 16 shows an exemplary embodiment of a completed reservoir.

FIG. 16 shows an exemplary embodiment of a completed reservoir 1600. The completed reservoir 1600 may have a reservoir casing 1602, a hollow area 1604, and an opening 1606. The opening 1606 may be large enough to allow liquid to flow through the opening, and/or may be fitted with or into a pump, filter, and/or valve.

After completion, the completed reservoir 1600 may be cleaned to remove residue or impurities. In an exemplary embodiment, the reservoir may be cleaned by injecting and removing hot water with a syringe. In other embodiments, cleaning may include submerging the reservoir in DI water and/or a detergent and/or by injecting and removing DI water with a syringe. It may be understood that this cleaning process may prevent unwanted particles from being included with the delivered medicine and from entering the human tissue/organ delivery site.

Discussing now the methods and systems for sensing volume with the exemplary reservoirs described. In an exemplary embodiment, the reservoir system may include a flowmeter as part of its integrated smart technology. The reservoir system may further include an embedded hardware and/or software platform which may calculate the instantaneous reservoir volume which may correspond to flow rates as needed.

In an exemplary embodiment, the reservoir may connect with a sensing system. The sensing system may, for example, measure ambient pressure and temperature of a gas volume that surrounds the reservoir inside the device case. From the pressure and temperature changes, the changes in gas volume may be strategically calculated to allow safe and effective reservoir monitoring like never before. Notably, the reservoir may be flexible while the outer case is rigid, therefore it may be understood that the volume change of the gas may directly correspond to the volume change of the payload fluid inside the reservoir, thereby allowing for real-time, around-the-clock monitoring of the reservoir volume state with high precision and low power consumption. It may be understood the sensing system may provide benefits in terms of safety and security for a device implanted within the human body for direct medicine delivery, especially for those sitting directly next to the brain.

In another exemplary embodiment a closed case pressure sensing system may be used. The closed case pressure sensing takes advantage of the change of air volume within a rigid container. The pressure sensor may be mounted within the free air space of the case. When the reservoir is full, it takes up more of the air space and results in a higher air pressure. When the reservoir is empty, it allows the air molecules to spread out more, resulting in a lower pressure. Therefore, a pressure-volume curve may be calculated that can be used to predict volume based on a known, measured pressure.

In another embodiment an in-line pressure sensor may be used. In the embodiment an in-line pressure sensor may be connected directly to the reservoir. It may be understandable that the in-line pressure sensor may take advantage of the inherent pressure-volume curve of the reservoir as the reservoir is filled with fluid. It may be understood that the pressure curve generated by the filling of the reservoir with fluid may be modeled, and volume of the reservoir may be used to determine pressure, and/or to give high/low pressure alerts. In an embodiment the in-line pressure sensor may be included directly on a medical device PCB or other medical device hardware, and may be connected to the reservoir via, for example, tubing or another semi-rigid or rigid connection.

Referring to FIGS. 17-21 the above volume sensing concepts may be illustrated. FIG. 17. may show an exemplary graph showing temperature/pressure over time with no fluid flow 1700. The graph 1700 may have a temperature axis 1702 and a time axis 1704. The graph 1700 may show that with no fluid flow the temperature remains substantially constant 1706. The graph 1700 may have a pressure axis 1708 and a time axis 1710. The graph 1700 may show that with no fluid flow the pressure remains substantially constant 1712.

Figure 18:
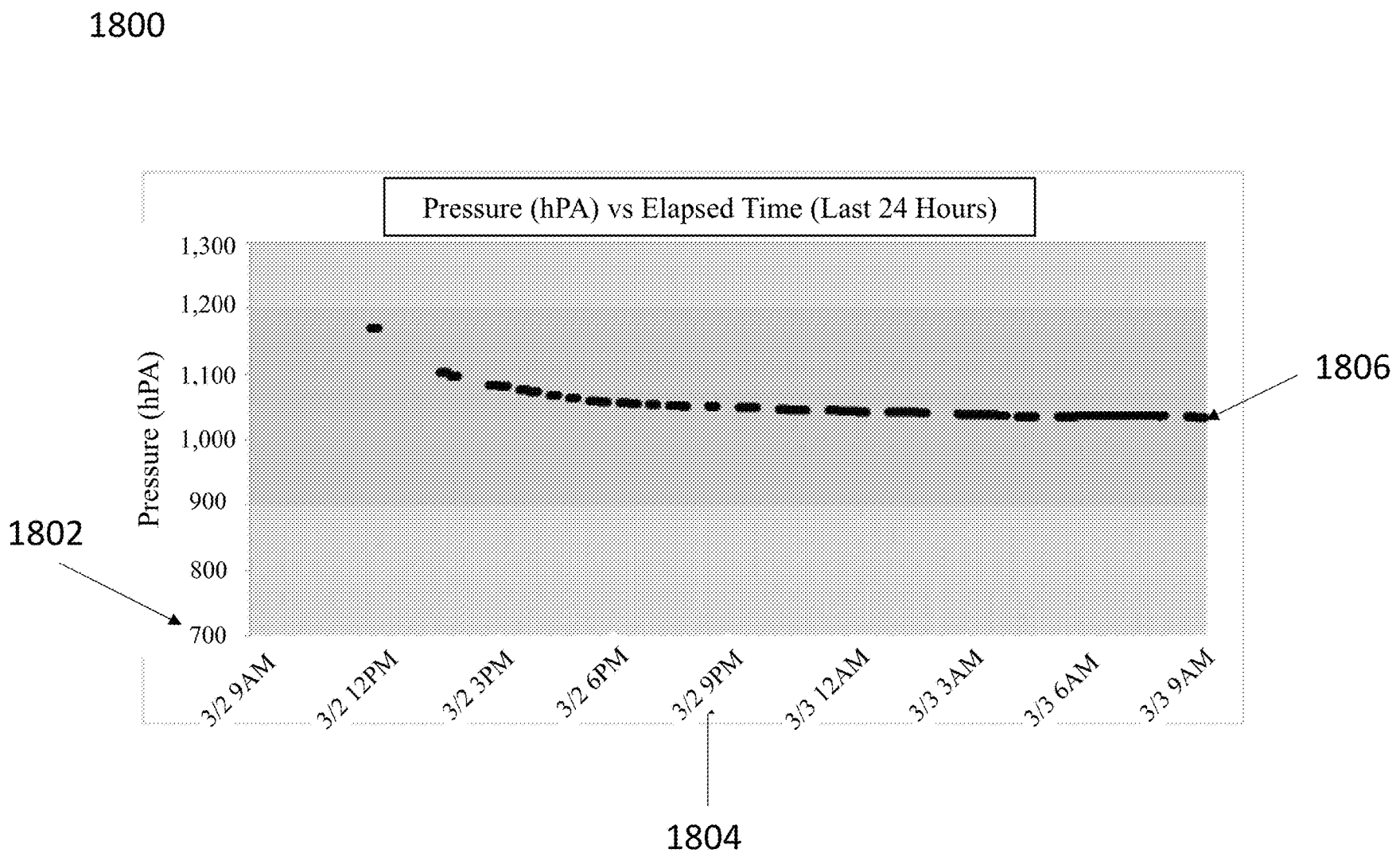

FIG. 18 may show an exemplary graph showing pressure over time with fluid flow 1800. The graph 1800 may have a pressure axis 1802 and a time axis 1804. The graph 1800 may show that as fluid flows from the reservoir the pressure may decrease 1806.

Figure 19:
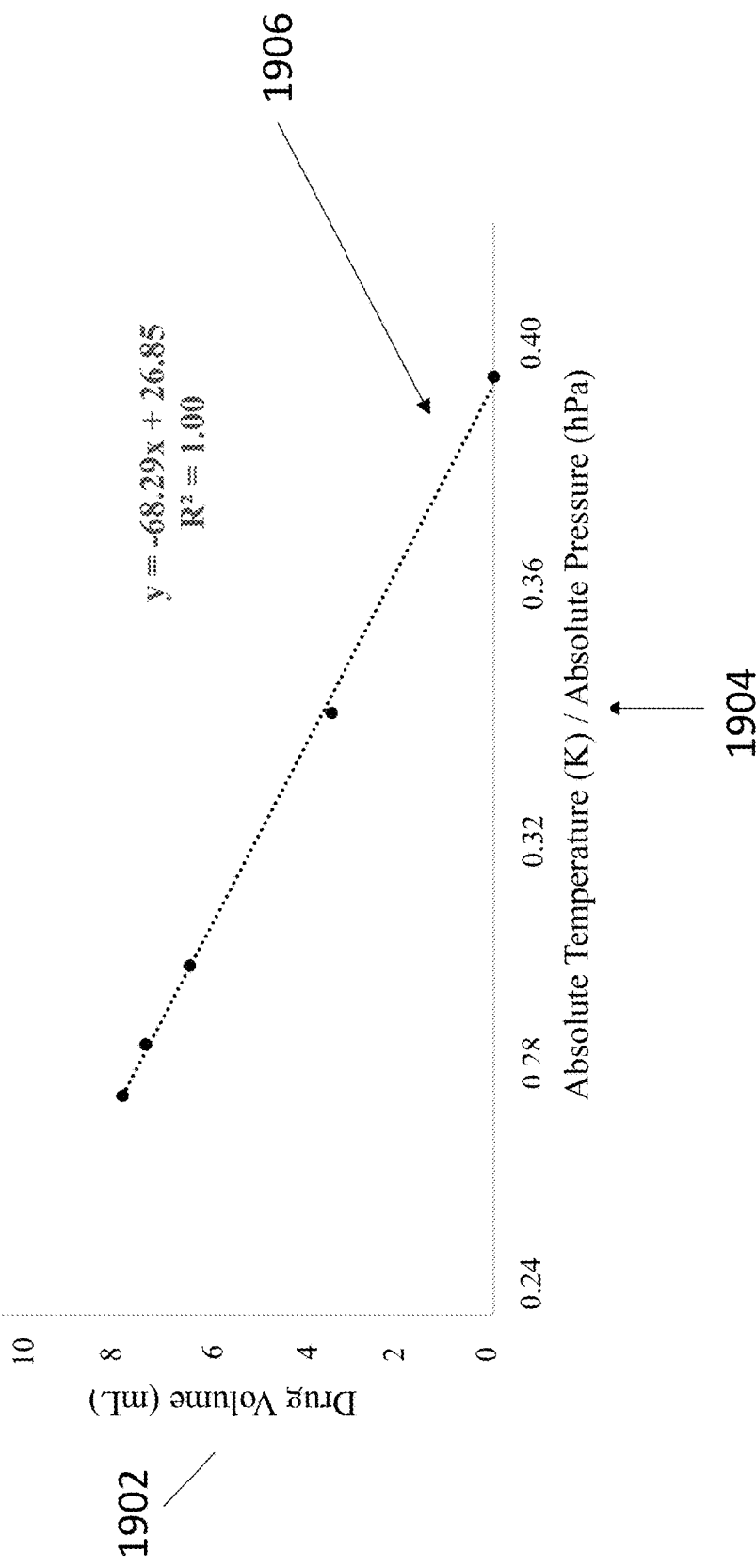
FIG. 19 shows an exemplary graph detailing the relationship between fluid volume and absolute temperature over absolute pressure.

FIG. 19 may show an exemplary graph detailing the relationship between fluid volume and the ratio of absolute temperature over absolute pressure 1900. The graph may have a drug volume axis 1902 and an axis that plots the absolute temperature divided by absolute pressure 1904. The graph may show that there is a linear relationship between the drug volume and the absolute temperature divided by absolute pressure 1906.

Figure 20:
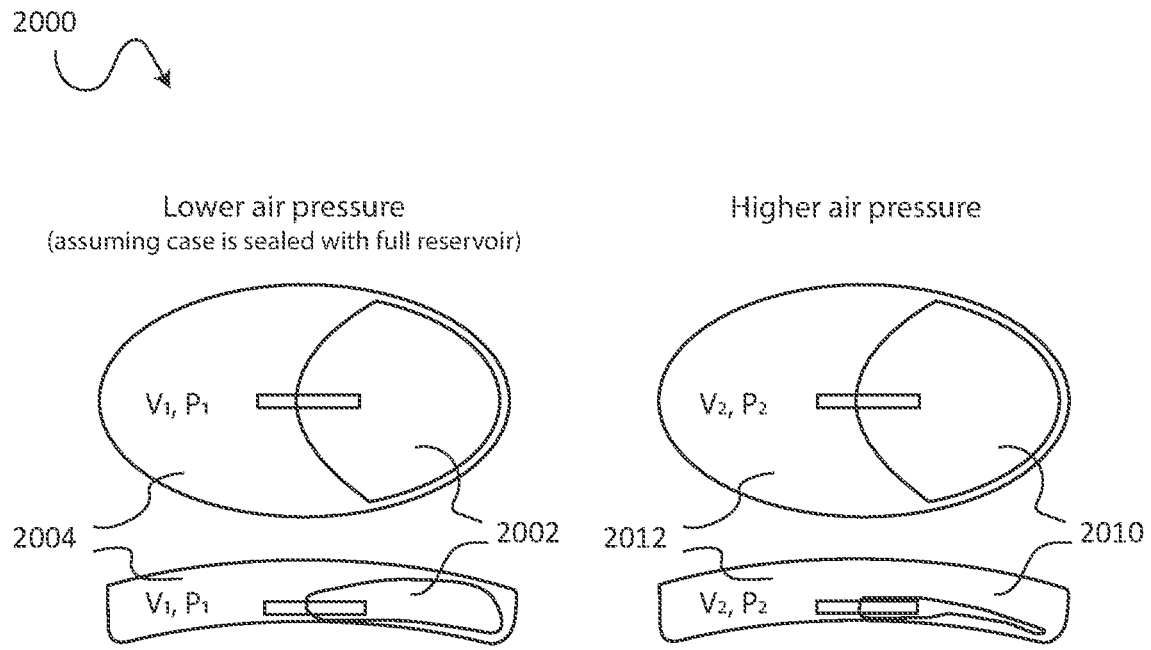
FIG. 20 shows three stages of an exemplary reservoir as fluid is dispensed from the reservoir.
Figure 21:
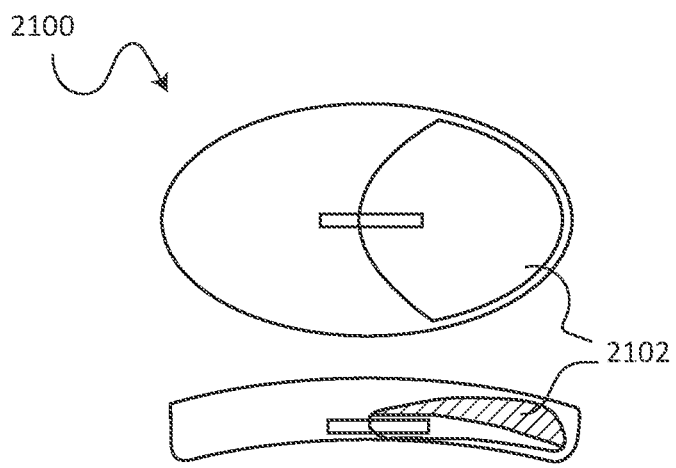
FIG. 21 shows the difference between an exemplary reservoir at lower air pressure and at higher air pressure.

FIG. 20 may show three stages of an exemplary reservoir as fluid is dispensed from the reservoir 2000. FIG. 21 may show the difference between an exemplary reservoir at lower air pressure and at higher air pressure. In a first stage there may be a full reservoir 2002, and a first air volume 2004 of the space around the reservoir may be minimized due to the volume of the reservoir being maximized. In a second stage there may be a half full 2006 or partially diminished reservoir. A second air volume 2008 may be larger than the first air volume 2004. In a third stage there may be an empty 2010 or nearly empty reservoir. A third air volume 2012 may be larger than the second air volume 2008. A difference between the full reservoir 2002 and the empty reservoir 2010 may be seen in, for example, an overlaid image 2102.

In yet another exemplary embodiment capacitance may be used to measure the volume of the reservoir. In a reservoir design where one side is fixed in place, as the reservoir expands the free side will change distance. Based on the distance between the capacitive plates, the output voltage will change, and the volume can be predicted. In yet another exemplary embodiment a light sensor may be used. Where the reservoir is opaque, an Infrared LED and photoresistor may be used to measure the volume. Based on the amount of light the sensor receives, the volume may be calculated. When the volume of liquid is high, the reservoir may be more open and there may be a larger pathway for more light to travel from the LED to the sensor. When the reservoir volume is low, the pathway may be more closed and the sensor may receive less light. This correlation may be used to make a model to predict reservoir volume based on a measured sensor voltage.

In an exemplary embodiment, the reservoir may be shaped so as to conform to the shape of a case or subcutaneous port and may ensure maximum utilization of available space within the implant. This unique design may allow many benefits including connectivity of several catheters (i.e. two in this embodiment for bilateral brain medicine delivery) and its unhindered shape may allow for optimized integration of embedded components so that no potential space remains unutilized and thus the device may fit optimally within the human head (i.e. without any visible deformity noticed from visual exam).

In an exemplary embodiment, the reservoir may be housed within an enclosed space, for example, it may be hermetically sealed (to air) within an alloplastic material or may be otherwise fully embedded in a biocompatible material (i.e. so that the air gas volume surrounding the reservoir remains fixed at all times). This may prevent the reservoir system from interacting with the patient's immune system and any fibrosis around it, which may prevent the reservoir system from being attacked by the immune system. It may also allow for a unique embedded sensor system to have indirect flowmetering capabilities, given that the air space expansion is directly in inverse proportion to volume taken up by the fluid-filled reservoir.

In an exemplary embodiment, the reservoir system within the alloplastic casing may be rigidly affixed to the skull where it is placed in the combined skull and soft tissue space. By being rigidly fixed to the system, free motion around the subcutaneous space may be prevented, which may drastically reduce the risk of deep infections in the patient. In some exemplary embodiments a high-profile circular ring for which palpation denotes needle placement may reach into the superficial soft tissue planes. If not, a low-profile ring around the reservoir-port system would fail to allow the healthcare provider safe and effective palpability and thus make injections unsafe for the patient. Some embodiments may allow for direct needle punctures and may alleviate the need for a distinct subcutaneous port, and thus the high-profile ring in the soft tissue space may instead move to an area directly over the reservoir.

In an exemplary embodiment, the reservoir may be refillable through the use of transcutaneous needles of special non-boring design (i.e. so as the reservoir material is not damaged permanently by a boring needle and can maintain integrity with necessary leak prevention), which may be able to refill the reservoir within several minutes. In an alternative embodiment, silicone sheets may be used, which may allow for "self-healing" of the reservoir through the silicone sheet walls. The "self-healing" zone may be integrated directly into the reservoir, which may reduce the device footprint and limit the overall number of components within the device.

In an exemplary embodiment, there may be a reservoir that has a reservoir body with a first end and a second end. The reservoir body may form an interior cavity, the interior cavity may be able to hold and contain a medicinal liquid for which extravasation is prevented in light of long-term storage. The first end may have a protrusion with an opening, the opening may be able to receive and dispense the liquid in a precise, controlled fashion and with the ability to work on or off at different time points throughout the day. Furthermore, the second end may have rounded edges and a three-dimensional shape, which may mitigate the size constraints presented by the human body and removes any form of visible deformity, and the first and second end may be cured or heat sealed together.

In some embodiments, the reservoir body may be configured to fit within an implantable medical device. In some embodiments, unhindered, unlimited, three-dimensional shape characteristics may be greatly beneficial to those human body devices where size constraints are challenging and wasted space internally could have dramatic, deformity-causing effects.

In some embodiments, the reservoir body may be formed from at least one of biocompatible silicone and three-dimensional printed, alloplastic material and may thereby be MRI-safe, MRI-compatible, and MRI-lucent, given the absence of ferrous containing elements.

In some embodiments, the reservoir body may be formed from one or more of biocompatible polyethylene, parylene, or a fluoroelastomer.

In some embodiments, the reservoir opening of the first end may be able to connect to a catheter.

In some embodiments, the opening of the first end is able to connect to a network of multiple catheters. Thus, a multi-catheter system reservoir system, as described here, allows the surgeon an unprecedented ability to place a single catheter into each brain lobe, and therefore deliver medicine bilaterally across the brain. Chronic diseases like Parkinson's, Alzheimer's, depression, etc. could all be treated in a novel, bilateral way.

In some embodiments, the opening of the first end may be able to connect to at least one of a pump, filter, or valve. Also, it may also connect to two pumps thereby allowing a total of four catheters.

In some embodiments, the medicinal liquid held by the inner cavity and received and dispensed by the opening may be a medicinal drug. It may also be an organ-enhancing natural occurring substance (as opposed to a man-made medicinal drug), like something to help improve brain function, reverse effects of aging, and/or stimulate newer brain tissue regeneration.

In an exemplary embodiment, the method for making a medicinal reservoir may include creating a core, casting a bottom layer of material in a reservoir mold, partially curing the bottom layer of material in the reservoir mold, placing the core on the partially cured bottom layer of material in the reservoir mold, casting a top layer of material over the partially cured bottom layer of material and core in the reservoir mold, fully curing the bottom and top layer of material in the reservoir mold to form a reservoir, creating an opening in one end of the reservoir, and removing the core from the reservoir.

In some embodiments, the method for making the medicinal reservoir may further involve forming the core from soy wax.

In some embodiments, the method for making the medicinal reservoir may further include forming the bottom layer of material and the top layer from at least one of biocompatible silicone and three-dimensional printed, alloplastic material.

In some embodiments, the method for making the medicinal reservoir may include forming the bottom layer of material and the top layer from one of biocompatible polyethylene, parylene, or a fluoroelastomer.

In some embodiments, the method for making the medicinal reservoir may include placing a shaft on the partially cured bottom layer of material before casting the top layer of material over the bottom layer of material to create the opening in one end of the reservoir and removing the shaft when the medicinal reservoir has been fully cured.

In some embodiments, the method for making the medicinal reservoir may include placing the fully cured reservoir in a bag and heating until the core is melted to remove the core from the reservoir and removing the wax core using a syringe through the opening in the one end of the reservoir such that no loose material is left in the reservoir.

In an exemplary embodiment, when the volume of the reservoir is emptied, the surrounding air pressure may be lowered. This may cause a range of vacuum pressures to be applied to the external surfaces of the reservoir. The pump may work against these pressures to deform the reservoir and pump fluid through the system.

The foregoing description and accompanying figures illustrate the principles, preferred embodiments, and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A medical implant reservoir comprising;
   a reservoir body consisting of a first side piece, a second side piece, and an inner fold piece; and
   a reservoir fitting;
   wherein, the first side piece is sealed with the second side piece with a top seal, a first side seal and a second side seal;
   the inner fold piece is sealed with the first side piece and the second side piece through a third side seal, a fourth side seal, and a bottom seal;
   the top seal includes a fitting opening; and
   the reservoir fitting is fit into the fitting opening;
   wherein the reservoir is adapted to be implanted within a human body.

2. The reservoir of claim 1, wherein the first and second side pieces and the inner fold piece are made from a reservoir material that is a metallized polymer film comprising at least a first layer of PET, and a second layer of LDPE; and the reservoir material is MRI-compatible and/or MRI-lucent.

3. The reservoir of claim 1, wherein the first and second side pieces and the inner fold piece are made from a reservoir material that is less than 10-thousandths of an inch thick.

4. The reservoir of claim 1, wherein the first side seal, the second side seal, the third side seal, the fourth side seal, the bottom seal, and the top seal are heat seals and the heat seals are 1-2 mm wide.

5. The reservoir of claim 1, wherein the reservoir fitting is 3-D printed out of a stereolithography resin and the reservoir fitting is bonded to the fitting opening by applying an adhesive.

6. The reservoir of claim 1, further comprising a volume sensing system, wherein the volume sensing system includes one or more of an in-line pressure sensor, a closed case pressure sensor, a capacitor sensor, and/or a light sensor.

7. The reservoir of claim 1, further comprising a rigid outer case surrounding the first side piece, the second side piece, and the inner fold piece; and a volume sensing system that measures a gas volume change of the reservoir body based on changes in an ambient pressure and a gas volume temperature in between the rigid outer case and the reservoir body.

8. The reservoir of claim 1, wherein the reservoir is adapted to be placed on a skull.

\* \* \* \* \*